United States Patent
Ochi et al.

(10) Patent No.: US 11,147,437 B1
(45) Date of Patent: Oct. 19, 2021

(54) TRIMMED IMAGER PROBE

(71) Applicant: Nanosurgery Technology Corporation, Sarasota, FL (US)

(72) Inventors: Sam Seiichiro Ochi, Lakewood Ranch, FL (US); Mark Walter, Sarasota, FL (US); Peter J. D'Aquanni, Murrieta, CA (US)

(73) Assignee: Nanosurgery Technology Corporation, Sarasota, FL (US)

( * ) Notice: Subject to any disclaimer, the term of this patent is extended or adjusted under 35 U.S.C. 154(b) by 442 days.

(21) Appl. No.: 16/016,471

(22) Filed: Jun. 22, 2018

Related U.S. Application Data

(60) Provisional application No. 62/524,310, filed on Jun. 23, 2017, provisional application No. 62/524,364, filed on Jun. 23, 2017.

(51) Int. Cl.
| | | |
|---|---|---|
| *A61B 1/05* | (2006.01) | |
| *A61B 1/06* | (2006.01) | |
| *A61B 1/07* | (2006.01) | |
| *A61B 1/00* | (2006.01) | |
| *A61B 17/34* | (2006.01) | |
| *A61B 1/317* | (2006.01) | |

(52) U.S. Cl.
CPC ............ *A61B 1/051* (2013.01); *A61B 1/0011* (2013.01); *A61B 1/00096* (2013.01); *A61B 1/00154* (2013.01); *A61B 1/0607* (2013.01); *A61B 1/07* (2013.01); *A61B 1/317* (2013.01); *A61B 17/3421* (2013.01)

(58) Field of Classification Search
CPC ... A61B 1/051; A61B 1/00096; A61B 1/0011; A61B 1/00154; A61B 1/0607; A61B 1/07; A61B 1/317; A61B 17/3421; A61B 17/3415
See application file for complete search history.

(56) References Cited

U.S. PATENT DOCUMENTS

| | | | | |
|---|---|---|---|---|
| 4,904,048 | A * | 2/1990 | Sogawa | A61B 1/0058 385/118 |
| 5,621,830 | A * | 4/1997 | Lucey | A61B 1/00179 385/118 |
| 5,647,840 | A * | 7/1997 | D'Amelio | A61B 1/00091 600/169 |
| 10,120,102 | B2 * | 11/2018 | Tsakalakos | G01V 9/005 |
| 2013/0172677 | A1 * | 7/2013 | Kennedy, II | A61B 1/0125 600/112 |
| 2017/0290492 | A1 * | 10/2017 | Hamm | A61B 1/00135 |
| 2017/0307872 | A1 * | 10/2017 | Hatase | A61B 1/0684 |
| 2018/0084986 | A1 * | 3/2018 | Ochi | A61B 1/015 |
| 2019/0004254 | A1 * | 1/2019 | Yoshino | G02B 6/3897 |
| 2020/0046213 | A1 * | 2/2020 | Bendory | A61B 1/0669 |

* cited by examiner

*Primary Examiner* — Timothy J Neal
*Assistant Examiner* — William B Chou

(57) ABSTRACT

An apparatus includes a trimmed imager including an imager chip and an encapsulation layer, the imager chip have a polygonal cross-section with a first number of corners, the encapsulation layer being disposed around the polygonal cross-section of the imager chip and having a second number of corners that is greater than the first number of corners; and a slotted tube having a plurality of first slots, the corners of the encapsulation layer being disposed in the plurality of first slots.

20 Claims, 11 Drawing Sheets

TRIMMED IMAGER PROBE

CROSS REFERENCE TO RELATED APPLICATIONS

This application claims the benefit of U.S. Provisional Patent Application No. 62/524,310, filed on Jun. 23, 2017, and of U.S. Provisional Patent Application No. 62/524,364, filed on Jun. 23, 2017, which are incorporated by reference herein for all purposes. A U.S. Nonprovisional patent application Ser. No. 16/016,464 entitled "SLOTTED IMAGING PROBE," filed with the U.S. Patent and Trademark Office on the same day as the present application on Jun. 22, 2018, and assigned to the same applicant as the present application, is also incorporated by reference herein for all purposes.

BACKGROUND

Surgical interventions provide significant mechanisms for diagnosing and treating disease, injuries, pain, and other medical problems. Surgical procedures, however, can cause problems of their own. For example, open surgical procedures often include forming large incisions, which can become infected, can cause pain, and/or can take a long time to heal. The various complications associated with open surgery can significantly impact a patient's quality of life, and can even cause permanent medical problems or even death. These complications can also increase the costs associated with medical care.

Minimally, or non-, invasive, procedures can be used to diagnose and treat the same medical problems as open procedures, without the same risk of complications. A surgeon performing a minimally invasive procedure on a patient can see and treat a therapeutic target by, inserting a camera and a surgical tool into the patient's body, and treating the therapeutic target remotely. Even when the tool is inserted through an incision, the incision is relatively small. As a result, large incisions—and the risks of large incisions—can be avoided.

Arthroscopy is a minimally invasive surgical procedure for diagnosing and treating problems inside of a patient's joint. Using arthroscopy, a surgeon can see an injury in a patient's knee by forming a small incision in the patient's skin, and inserting a device known as an "arthroscope" through the incision. The arthroscope includes a camera, which enables the surgeon to see whether any tissues (e.g., cartilage, ligaments, bone, etc.) within the knee are damaged. The damaged tissue can then be treated, repaired, or both.

Because a substantial portion of minimally invasive procedures require operators to remotely view structures beneath skin, many minimally invasive devices include imaging devices. In particular, semiconductor imaging devices can be used in a variety of minimally invasive devices, such as arthroscopes, to produce digital images or video that can be displayed to an operator during a minimally invasive procedure.

However, existing imaging devices are too large to be incorporated into certain next-generation minimally invasive devices.

SUMMARY

According to various embodiments, an apparatus includes a trimmed imager including an imager chip and an encapsulation layer, the imager chip have a polygonal cross-section with a first number of corners, the encapsulation layer being disposed around the polygonal cross-section of the imager chip and having a second number of corners that is greater than the first number of corners; and a slotted tube having a plurality of first slots, the corners of the encapsulation layer being disposed in the plurality of first slots.

In some embodiments, the imager chip has a square cross-section.

In some embodiments, the imager chip is configured to capture digital images through a distal end of the slotted tube.

In some embodiments, an outer surface of the encapsulation layer has a plurality of curved sides.

In some embodiments, the corners of the imager chip are disposed in the plurality of first slots.

In some embodiments, the apparatus further includes a plurality of light guides, wherein the slotted tube includes a plurality of second slots, the plurality of light guides being disposed in the plurality of second slots, respectively.

In some embodiments, the apparatus further includes an interposer disposed in the slotted tube and proximate to the trimmed imager, the interposer being configured to supply a voltage to the imager chip and to receive image data from the imager chip.

In some embodiments, the apparatus further includes a lens disposed on a distal end of the slotted tube, the lens being configured to focus light on the imager chip.

According to various embodiments, a method includes locating a border between an imager chip and an encapsulation layer, an imager including the imager chip and the encapsulation layer; generating a trimmed imager by removing portions of the encapsulation layer without removing portions of the imager chip using the located border; and inserting the trimmed imager into a slotted tube, a plurality of corners of the trimmed imager being disposed in slots of the slotted tube.

In some embodiments, locating a border between the imager chip and the encapsulation layer includes performing a computed tomography (CT) scan on the imager, the imager chip and the encapsulation layer having different levels of x-ray attenuation.

In some embodiments, locating a border between the imager chip and the encapsulation layer includes locating a center of the imager chip, and measuring a predetermined dimension of the imager chip from the located center.

In some embodiments, generating the trimmed imager by removing portions of the encapsulation layer without removing portions of the imager chip using the located border includes cutting portions of the encapsulation layer, sawing portions of the encapsulation layer, grinding portions of the encapsulation layer, or a combination thereof.

In some embodiments, generating the trimmed imager by removing portions of the encapsulation layer without removing portions of the imager chip using the located border includes: removing first portions of the encapsulation layer by cutting the encapsulation layer without cutting the imager chip; removing second portions of the encapsulation layer by grinding the encapsulation layer with a first grinder without grinding the imager chip; and removing third portions of the encapsulation layer by grinding the encapsulation layer with a second grinder without grinding the imager chip, the second grinder having a smaller diameter than the first grinder.

In some embodiments, removing the second portions of the encapsulation layer by grinding the encapsulation layer with the first grinder without grinding the imager chip includes positioning the first grinder a buffer distance from a corner of the located border, and removing the third portions of the encapsulation layer by grinding the encapsulation layer with the second grinder without grinding the imager chip includes positioning the second grinder the buffer distance from a side of the located border.

In some embodiments, the buffer distance is about 10 nanometers.

In some embodiments, the method includes gluing the trimmed imager to the slotted tube.

According to various embodiments, an apparatus includes a needle; and a probe disposed in the needle, the probe including: a trimmed imager including an imager chip and an encapsulation layer, the imager chip have a polygonal cross-section with a first number of corners, the encapsulation layer being disposed around the polygonal cross-section of the imager chip and having a second number of corners that is greater than the first number of corners; and a slotted tube having a plurality of first slots, the corners of the encapsulation layer being disposed in the plurality of first slots.

In some embodiments, the probe further includes a plurality of light guides, and the slotted tube includes a plurality of second slots, the plurality of light guides being disposed in the plurality of second slots, respectively.

In some embodiments, the apparatus further includes a bulb attached to a proximal end of the needle and a proximal end of the probe; and a hub disposed on the bulb, the hub being configured to extend and retract a distal end of the probe from a distal end of the needle.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

DETAILED DESCRIPTION

Figure 1A:
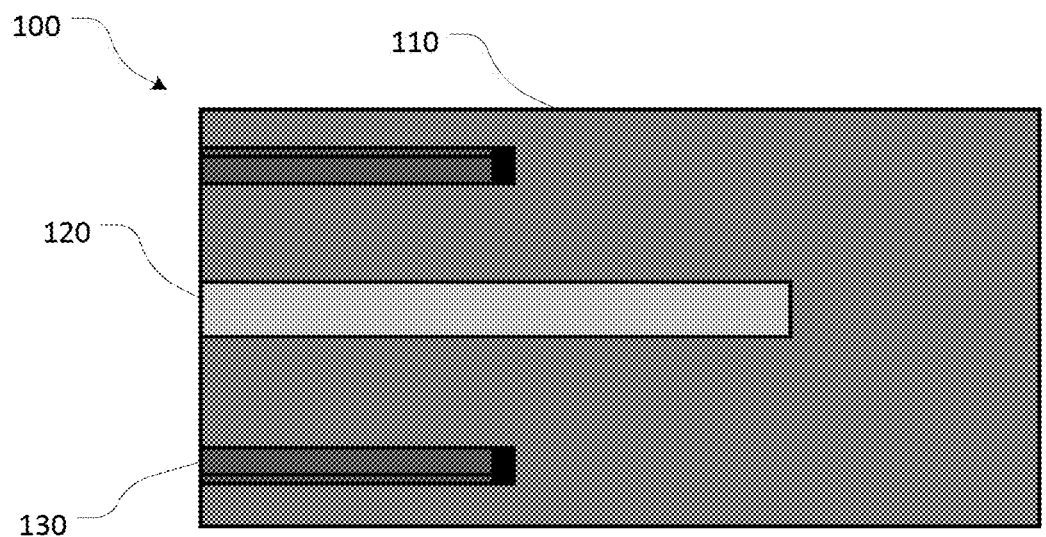
FIGS. 1A and 1B illustrate an imaging probe according to an embodiment of the present disclosure.

Throughout the present disclosure, reference is made to particular features of various embodiments of the invention. Embodiments of the invention encompass all possible combination of the disclosed features. For example, where a particular feature is disclosed in the context of a particular aspect, implementation, or embodiment, or is disclosed in a particular claim, that feature can also be used, to the extent possible, in combination with and/or in the context of any other aspect, implementation, or embodiment.

When a method or process including two or more defined steps is described herein, the defined steps can be carried out in any order or simultaneously, except where the context excludes that possibility. For example, a disclosed method including defined steps can include one or more steps carried out before the defined steps, can include one or more steps carried out after the defined steps, can include one or more steps carried out between the defined steps, or a combination thereof.

The terms "comprises" and "includes," as well as their grammatical equivalents, indicate that other components, ingredients, steps, etc. are optionally present. For example, an article "comprising" components A, B, and C, can consist of only components A, B, and C, or can contain not only components A, B, and C, but also one or more other components.

The terms "cubic" or "cuboid" each indicate a prism having a square cross-section that is perpendicular to the joining edges of the prism. As used herein, a cubic or cuboid shape is not necessarily a right prism having two base faces that are perpendicular to the joining edges. Furthermore, as used herein, the faces of a cubic or cuboid are not necessarily square. For example, the faces of the cubic or cuboid shape can be rectangular.

The terms "proximate" and "distal," as well as their grammatical equivalents, indicate a relative position. As used herein, a "proximate" structure can be considered a "distal" structure, when a "distal" structure is considered a "proximate" structure.

A probe for imaging features underneath a patient's skin includes an imager inside of a tube, e.g., a rigid, cylindrical tube. When the probe is inserted underneath the patient's skin, the imager images the features through a distal end of the tube.

The imager, however, is not necessarily the same shape as the tube. For example, the imager may be cubic, such that when the imager is placed inside of the tube and the corners of the imager abut against the inner surface of the tube, four empty spaces are formed between sides of the imager and the inner surface of the tube. In this configuration, the inner surface of the tube has to be at least as wide as a diagonal width of the imager.

According to embodiments of the present disclosure, portions of an encapsulation layer are trimmed from the imager. Due to the trimmed portions of the encapsulation layer, an outer surface of the imager more closely approximates a cylinder, even though an imager chip in the imager has a polygonal cross-section.

Corners of the trimmed imager are arranged within slots in wall of the tube, which minimizes empty spaces between the trimmed imager and the tube. Other structures in the probe, such as light guides, can also be arranged in slots in the tube. Due to the slots in the tube, the width of the probe can be minimized.

Figure 1B:
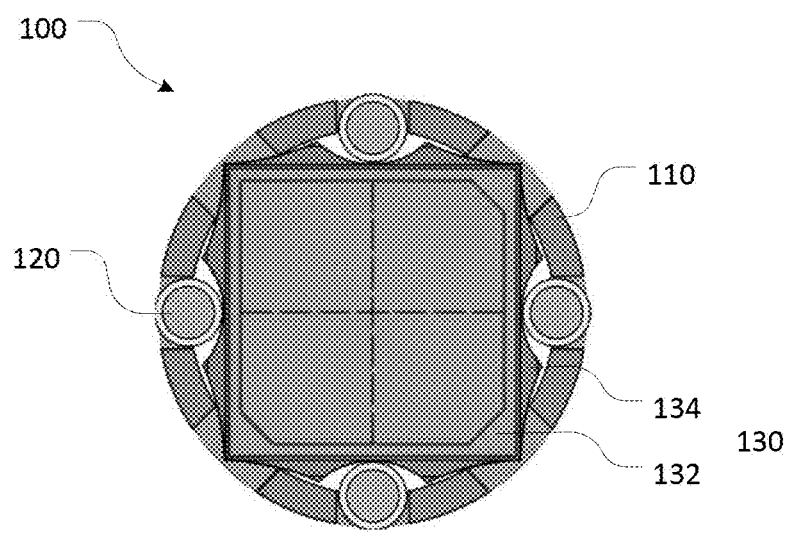

FIGS. 1A and 1B illustrate an imaging probe 100 according to an embodiment of the present disclosure. The imaging probe 100 includes a slotted tube 110, a plurality of light guides 120, and a trimmed imager 130.

The slotted tube 110 is a cylindrical tube that partially encloses the plurality of light guides 120 and the trimmed imager 130. A plurality of slots are located in a wall of the slotted tube 110. The light guides 120 are threaded through some of the plurality of slots, and corners of the imager 130 are threaded through the other plurality of slots. Because of the slots, the slotted tube 110 is able to accommodate the trimmed imager 130 even though a diagonal width of the trimmed imager 130 is longer than the inner width of the slotted tube 110. In some embodiments, the slotted tube includes a rigid material, such as stainless steel, a polymer, carbon fiber, or a combination thereof.

The plurality of light guides 120 are configured to emit light that illuminates an area being imaged by the imager 130. The illumination provided by the plurality of light guides 120 can improve the quality of images or video acquired by the trimmed imager 130. The light guides 120 are substantially cylindrical and parallel to the slotted tube 110. In some embodiments, the plurality of light guides 120 are fiber-optic cables.

The trimmed imager 130 includes an imager chip 132 and an encapsulation layer 134, which is disposed around the imager chip 132. The imager chip 132 has a polygonal cross-section, such as a square cross-section. The encapsulation layer 134 is disposed on an outer surface of the imager chip 132. An outer surface of the encapsulation layer 134 is shaped differently than the outer surface of the imager chip 132. Specifically, the encapsulation layer has more corners than the imager chip 132, more sides than the imager chip 132, and more closely approximates a cylinder than the imager chip 132. In some embodiments, the outer surface of the imager chip 132 has flat sides, and the outer surface of the encapsulation layer 134 has curved sides.

The imager chip 132 is configured to acquire images and/or video of areas surrounding the imaging probe 100, from the perspective of the imaging probe 100. For example, the imager chip 132 is a digital camera that captures images and/or video in the form of digital images, and that outputs image data representing the digital images in the form of electrical signals.

The encapsulation layer 134 is configured to provide physical stability to the imager chip 132. In some embodiments, the encapsulation layer 134 electrically shields the imager chip 132.

In various embodiments, the imager chip 132 and the encapsulation layer 134 include different materials. For example, the imager chip 132 includes a plurality of semiconductor-based integrated circuits (ICs), e.g., silicon chips, and the encapsulation layer 134 includes a polymer-based material. The different materials in the imager chip 132 and the encapsulation layer 134 have different levels of x-ray attenuation, in some embodiments. Accordingly, when imaged using an x-ray-based imaging modality, such as computed tomography (CT), the imager chip 132 and the encapsulation layer 134 are distinguishable from each other.

The trimmed imager 130 is disposed in the slotted tube 110. Because the shape of the outer surface of the encapsulation layer 134 more closely approximates a cylinder than the imager chip 134, the trimmed imager 130 can fit snuggly inside of the slotted tube 110. That is, the shape of the encapsulation layer 134 minimizes empty space between the trimmed imager 130 and the slotted tube 110.

The trimmed imager 130 flanked on multiple sides by the light guides 120. The light guides 120 are configured to illuminate an area being imaged by the imager chip 132. For example, the light guides 120 are fiber-optic cables whose proximal ends are attached to one or more light emitting diodes (LEDs).

Although the slotted tube 110 is cylindrical, the trimmed imager 130 is not. In various embodiments, the slotted tube 110 has a circular cross-section, but the trimmed imager 130 has a cross-section with corners. In some embodiments, the broadest corners of the trimmed imager 130, i.e., the corners disposed the farthest from the center of the trimmed imager 130, are disposed radially from the corners of the imager chip 132.

As illustrated in FIGS. 1A and 1B, the corners of the trimmed imager 130 fit into some of the slots of the slotted tube 110, whereas other portions of the trimmed imager fit inside of the inner surface of the slotted tube 110. Other slots in the slotted tube accommodate the light guides 120, which are disposed, threaded, or otherwise present in the slots. In some embodiments, the slots through which the light guides 120 are threaded are wider and longer than the slots through which the corners of the trimmed imager 130 are disposed. That is, the slots accommodating the light guides 120 extend farther from a distal end of the slotted tube 110 than the slots accommodating the corners of the trimmed imager 130.

Although not illustrated, in some embodiments, the trimmed imager 130 and the light guides 120 are attached to the slotted tube 110 with a glue that is disposed inside of the slots. In certain embodiments, the imager 130 is held in place with respect to the slotted tube 110 by a structure that generates a frictional force between the imager and the slotted tube 110, e.g., a device including a spring.

Due to the shape of the encapsulation layer 134 and the slots in the slotted tube 110, the imaging probe 100 has a smaller diameter than other probes that accommodate the same imager chip 132.

Figure 2:
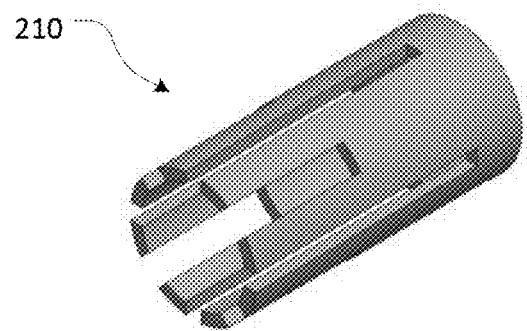
FIG. 2 illustrates a slotted tube according to an embodiment of the present disclosure.

FIG. 2 illustrates a slotted tube 210 according to an embodiment of the present disclosure.

The slotted tube 210 is cylindrically shaped. A plurality of slots extend in the wall of the slotted tube 210 from a distal end of the slotted tube 210. As illustrated, the slotted tube 210 includes four slots that can accommodate four light guides, and four slots that can accommodate four corners of an imager.

In some embodiments, the slotted tube 210 is a metal tube, such as a stainless steel tube. For example, the slotted tube 210 is a blunt, 18 gauge needle.

The slots in the slotted tube 210 have various shapes and lengths depending on the shapes of the light guides and the imager that fit into the slots. For example, the slots are rectangular openings in the wall of the slotted tube 210, as illustrated in FIG. 2.

Figure 3A:
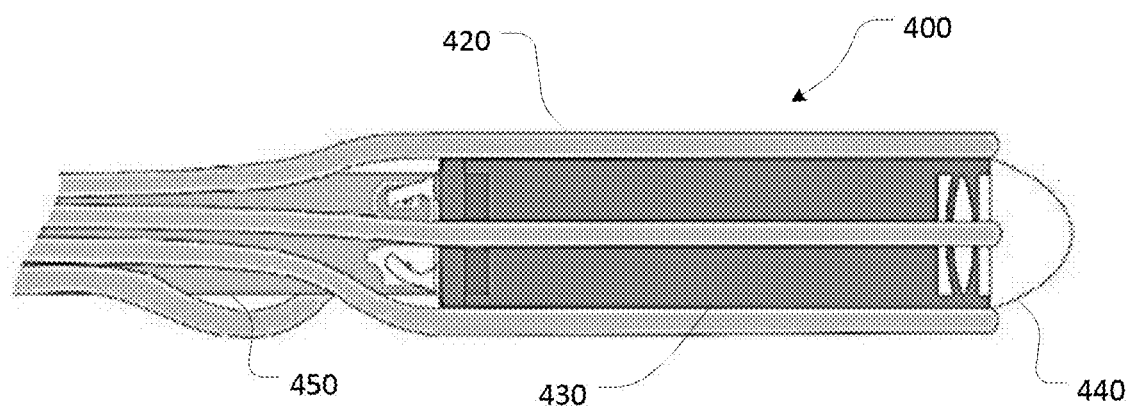
FIGS. 3A and 3B illustrate an imager assembly according to an embodiment of the present disclosure.
Figure 3B:
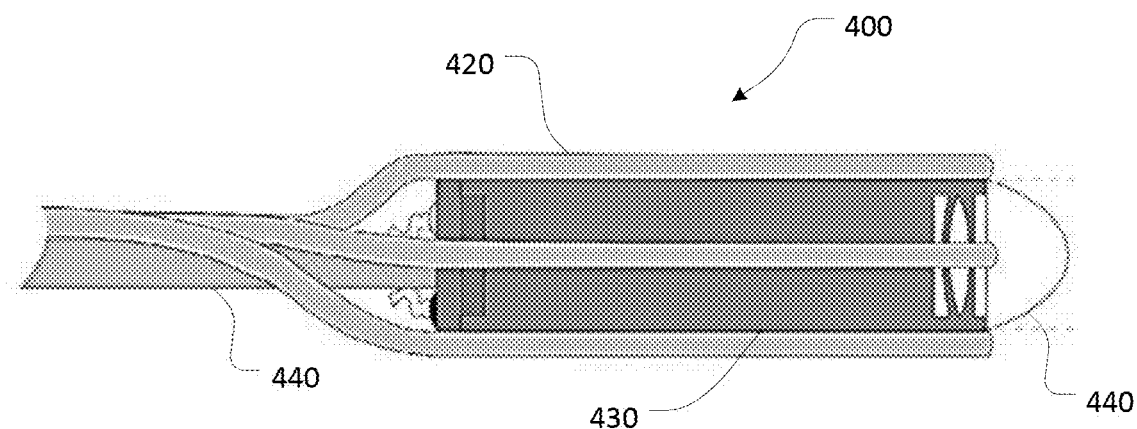

FIGS. 3A and 3B illustrate an imager assembly 300 according to an embodiment of the present disclosure. The imager assembly 300 includes a plurality of light guides 320, an imager 330, a lens 340, and an interposer 350.

The light guides 320 extend along outer surfaces of the imager 330, and are configured to illuminate spaces and structures being imaged by the imager 330. In various embodiments, each light guide 320 is disposed along a different surface of the imager 330.

The imager 330 is configured to capture images, video, or both. The imager 330 includes a plurality of image sensors respectively corresponding to a plurality of pixels. In some embodiments, the imager 350 has a plurality of corners, and is a trimmed imager, such as the trimmed imager 130 described above with respect to FIGS. 1A and 1B.

The lens 340 is configured to focus light on the image sensors in the imager 330. The lens 340 extends from a distal end of the imager 330.

The interposer 350 is disposed proximate to the imager 330, and is configured to electrically connect to the light guides 320 and the imager 330 via a plurality of leads. For example, the interposer 350 supplies power to the imager 330 and the light guides 320. In some embodiments, the interposer 350 supplies control signals to the imager 330, and receives image data from the imager 330 in the form of electrical signals.

In some embodiments, the imager assembly 300 is assembled with a slotted tube, such as any of the slotted tubes 110 and 210 described above. For example, the light guides 320 and corners of the imager 330 are disposed in slots of the slotted tube, the lens 340 extends from a distal end of the slotted tube, and the interposer 350 is disposed inside of the slotted tube.

Figure 4:
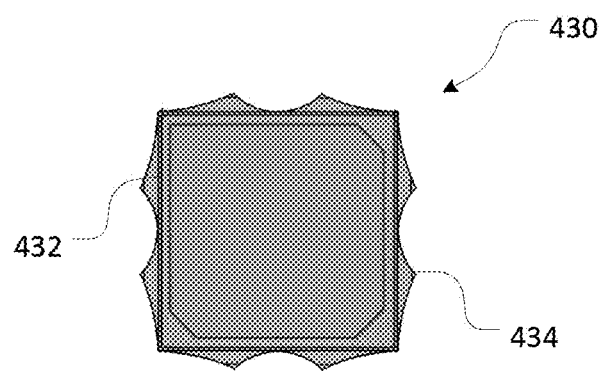
FIG. 4 illustrates a trimmed imager according to an embodiment of the present disclosure.

FIG. 4 illustrates a trimmed imager 430 according to an embodiment of the present disclosure. The trimmed imager 430 includes an imager chip 432 and a trimmed encapsulation layer 434.

The imager chip 432 is configured to capture images and/or video from inside of an imager probe, for example. However, the imager chip 432 has a polygonal cross-section with a plurality of corners. For example, as illustrated in FIG. 4, the imager chip 432 has a square cross-section with four corners.

The encapsulation layer 434 is disposed radially around the imager chip 432, and provides physical and electrical stability, for example. However, an outer surface of the encapsulation layer 434 does not have a polygonal cross-section, like the outer surface of the imager chip 434. Instead, the encapsulation layer 434 has more sides and more corners than the imager chip 432, allowing it to more closely fit inside of a cylindrical tube than the imager chip 432. In some embodiments, the encapsulation layer 434 has curved sides.

Due to the shape of the outer surface of the encapsulation layer 434, the trimmed imager 430 can fit into a relatively small cylindrical tube, and can therefore provide a relatively small imager probe.

Figure 5A:
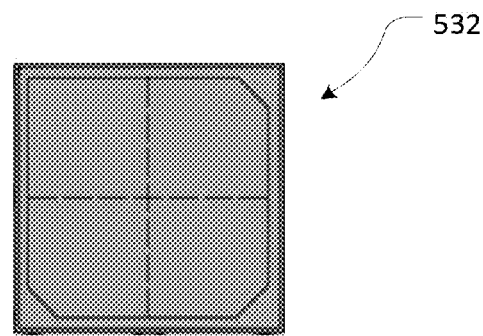
FIGS. 5A and 5B illustrate an imager chip according to an embodiment of the present disclosure.
Figure 5B:
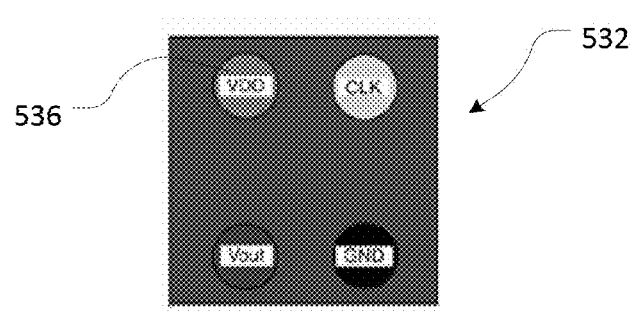

FIGS. 5A and 5B illustrate an imager chip 532 according to an embodiment of the present disclosure. A plurality of contacts 536 are disposed on a proximal end of the imager chip 532.

The imager chip 532 is configured to capture images and/or video, and output image data through the plurality of contacts 536 based on the captured images and/or video. In some embodiments, the imager chip 536 is a digital image sensor. For example, the imager chip 532 is a Camera-CubeChip manufactured by Omnivision.

The plurality of contacts 536 are configured to supply the imager chip 532 with a voltage that powers the imager chip 532, to supply a clock signal used by the imager chip 532, and to receive image data from the imager chip 532 in the form of electrical signals output by the imager chip 532.

The plurality of contacts 536 include an input voltage contact VDD, a clock contact CLK, an output voltage contact Vout, and a ground contact GND. The input voltage contact VDD supplies a voltage used to power the imager chip 532. The clock contact CLK supplies a clock signal to the imager chip 532. The output voltage contact Vout receives image data from the imager chip 532 in the form of electrical signals. The image data includes the images and/or video captured by the imager chip 532 that has been encoded into the electrical signals. The ground contact GND supplies a ground voltage to the imager chip 532.

Although not illustrated, the plurality of contacts 536 can be electrically connected to an interposer that has a plurality of corresponding contacts. In some embodiments, the imager chip 532 is part of a trimmed imager, which is disposed in a slotted tube.

Figure 6:
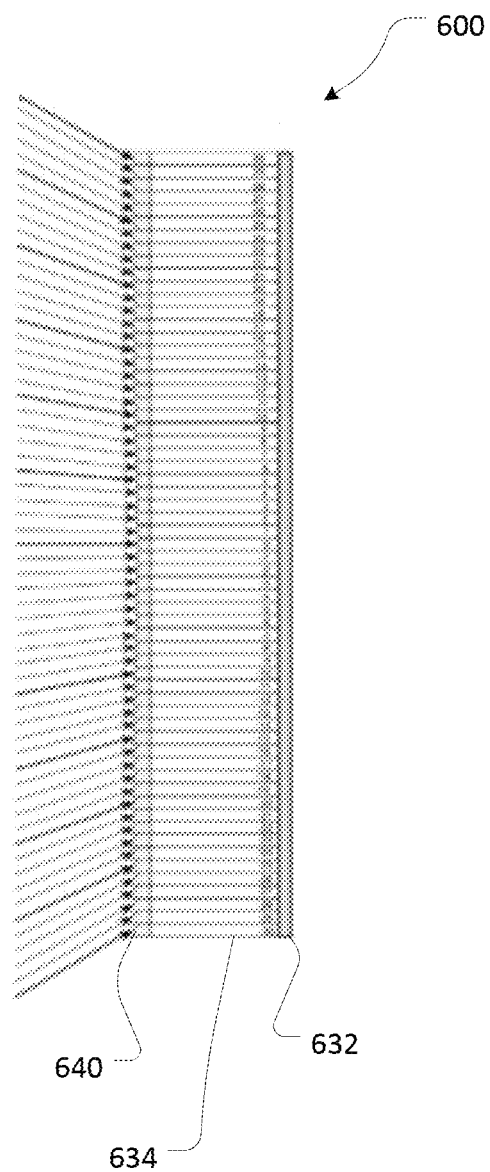
FIG. 6 illustrates a bee-eye imager according to an embodiment of the present disclosure.

FIG. 6 illustrates a bee-eye imager 600 according to an embodiment of the present disclosure. The bee-eye imager 600 includes an image sensor array 632, a plurality of light tubes 634, and a lens 640. In some embodiments, the image sensor array 632 and the plurality of light tubes 634 comprise the imager chip 532 described above with reference to FIGS. 5A and 5B.

The image sensor array 632 includes a plurality of image sensors arranged in rows and columns. With reference to FIG. 6, the rows extend in a depth direction and the columns extend in a vertical direction. Each one of the plurality of image sensors corresponds to a pixel. In some embodiments, each of the image sensors is a semiconductor device including a plurality of semiconductor layers. For example, each of the image sensors is a complementary metal oxide semiconductor (CMOS) image sensor.

The plurality of light tubes 634 direct light to the plurality of image sensors in the image sensor array 632, respectively, from the lens 640.

The lens 640 focuses light on the image sensor array 632. The lens 640 is a Fresnel lens, for example.

FIGS. 7A to 7E illustrate tip views of a trimmed imager during a fabrication method according to an embodiment of the present disclosure.

Figure 7A:
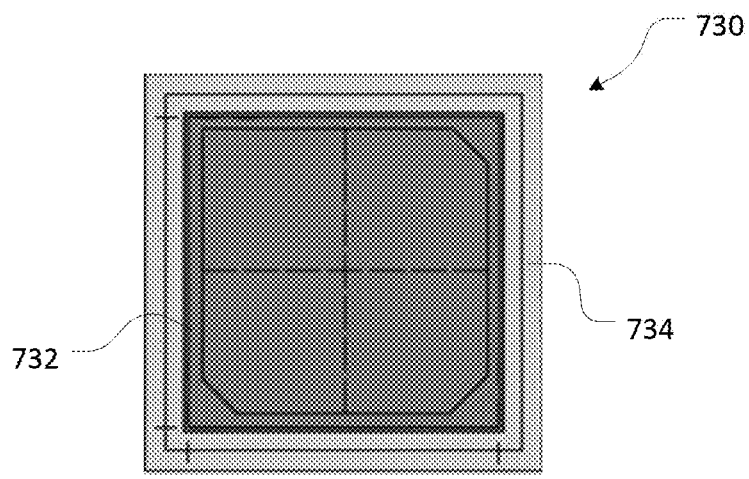
FIGS. 7A to 7E illustrate a process of fabricating a trimmed imager according to an embodiment of the present disclosure.

FIG. 7A illustrates an imager 730 according to an embodiment. The imager 730 includes an imager chip 732 and an encapsulation layer 734 disposed around the imager chip 732. The imager chip 732 has a polygonal cross-section. As illustrated in FIG. 7A, the encapsulation layer 734 has an even thickness around the imager chip 732, such that an outer surface of the encapsulation layer 734 is substantially similar in shape to the outer surface of the imager chip 732. The encapsulation layer 732 has first corners that extend radially from the corners of the imager chip 732.

As illustrated in FIG. 7A, the imager chip 732 has a square cross-section, but in some embodiments, the imager chip 732 has a differently shaped cross-section. The imager 730 illustrated in FIG. 7A is, for example, a Camera-CubeChip manufactured by Omnivision.

In some embodiments, the imager 730 is visualized using a computed tomography (CT) scan. The imager chip 732 and the encapsulation layer 732 include different materials, with different levels of x-ray attenuation. Accordingly, a CT scan of the imager 730 can be used to precisely locate the border between the imager chip 732 and the encapsulation layer 732.

In certain embodiments, the border between the imager chip 732 and the encapsulation layer 734 is located by locating a center point of the imager chip 732, and referring to predetermined dimensions of the imager chip 732. In some cases, the imager chip 732 is manufactured to within a tolerance of less than ten nanometers of the predetermined dimensions, which are supplied from the manufacturer. Accordingly, the border between the imager chip 732 and the encapsulation layer 734 can be precisely estimated.

The location of the border between the imager chip and the imager chip 732 and the encapsulation layer 734 is used in subsequent steps of the fabrication method to remove portions of the encapsulation layer 734 without removing portions of the imager chip 732.

Figure 7B:
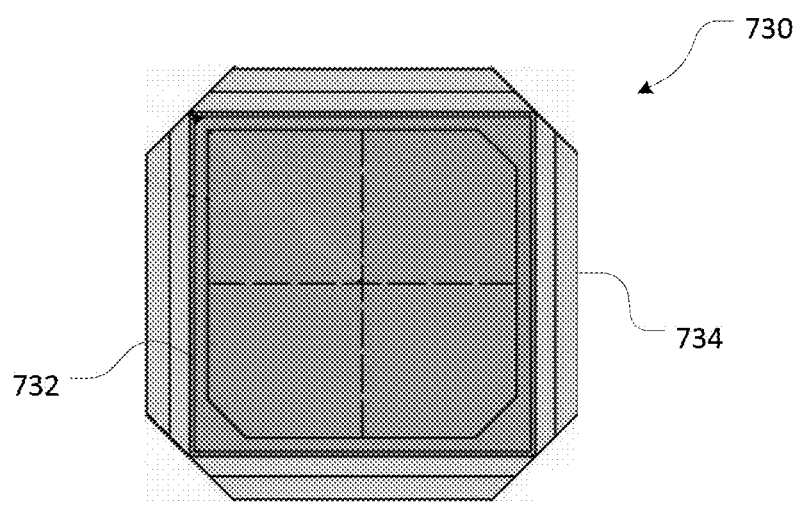

FIG. 7B illustrates the imager 730 with trimmed first corners according to an embodiment. The first corners have been sawed off of the encapsulation layer 734, for example. However, the imager chip 732 remains entirely intact. Portions of the encapsulation layer 734 are removed without trimming any portion of the imager chip 732 by referring to the border located or estimated between the imager chip 732 and the encapsulation layer 734. As illustrated in FIG. 7B, by trimming the first corners from the encapsulation layer 734, second corners of the encapsulation layer 734 are formed.

Figure 7C:
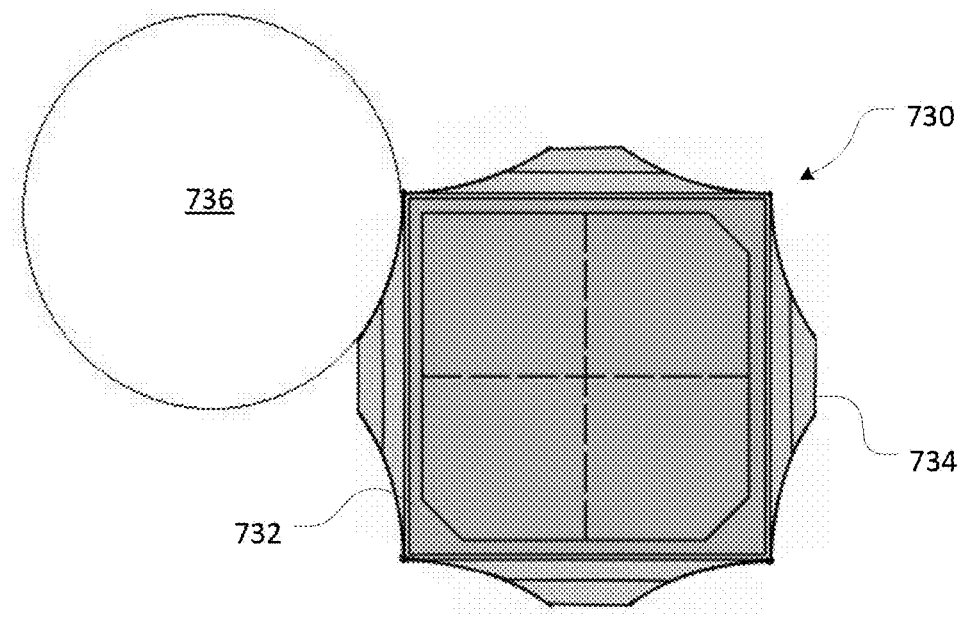

FIG. 7C illustrates the imager 730 trimmed by a first grinder 736 according to an embodiment. The grinder 736 removes portions of the encapsulation layer 734 without removing portions of the imager chip 732 by referring to the border between the imager chip 732 and the encapsulation layer 734. For example, the first grinder 736 is positioned such that it is spaced apart from the imager chip 732 by a buffer distance. In some embodiments, the buffer distance is about 10 nanometers or less.

As illustrated in FIG. 7C, the first grinder 736 removes eight portions of the encapsulation layer 734. Each corner of the imager chip 732 is adjacent to two portions of the encapsulation layer 734 that are removed by the first grinder 736.

Figure 7D:
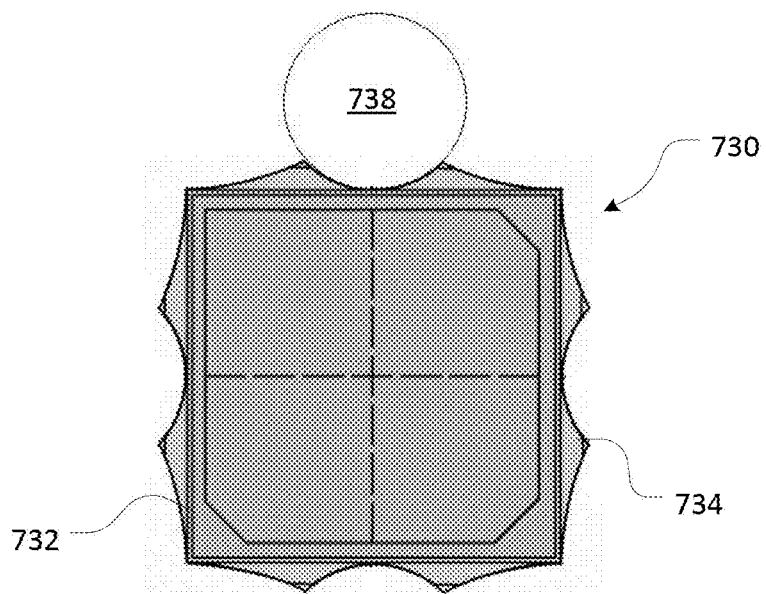

FIG. 7D illustrates the imager 730 trimmed by a second grinder 738 according to an embodiment. The grinder 738 removes portions of the encapsulation layer 734 without removing portions of the imager chip 732 by referring to the border between the imager chip 732 and the encapsulation layer 734. For example, the second grinder 738 is positioned such that it is spaced apart from the imager chip 732 by a buffer distance. In some embodiments, the buffer distance is 10 nanometers or less.

As illustrated in FIG. 7D, the second grinder 738 removes four portions of the encapsulation layer 734. Each portion removed by the second grinder 738 is adjacent to the center of a corresponding one of the four sides of the imager chip 732.

After the imager 730 has been trimmed by the second grinder 738, the imager 730 has a plurality of corners. In some embodiments, prominent corners of the imager 730 correspond to the corners of the imager chip 732 itself.

Figure 7E:
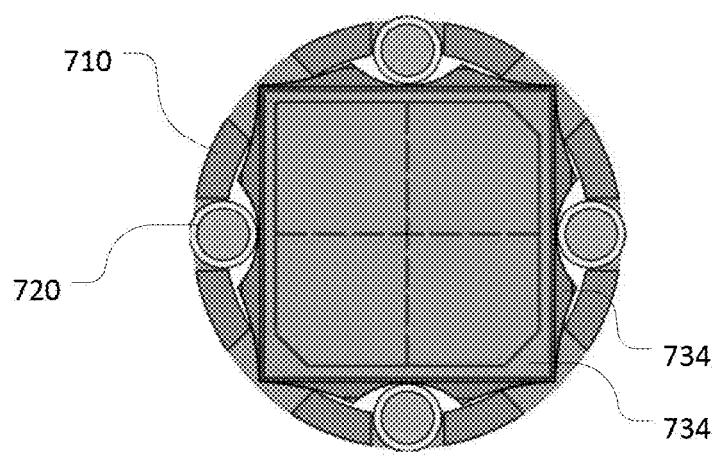

FIG. 7E illustrates the trimmed imager 730 mounted in a slotted tube 710. The corners of the imager 730 corresponding to the corners of the imager chip 732 are disposed in a first set of slots in the slotted tube 710. A plurality of light guides 720 are disposed in other slots in the slotted tube. In some embodiments, the trimmed imager 730, the slotted tube 710, and the light guides 720 are part of an imaging probe. Although not illustrated, the trimmed imager 730 and the light guides are attached to the slotted tube 710 using, for example, a glue disposed in the slots of the slotted tube 710.

In a specific embodiment, the imager 730 starts out with a cross-section having a size of 670 microns by 670 microns. In this embodiment, the first corners of the imager 730 are removed by performing 45 degree cuts with respect to the sides of the imager 730, where the cuts are distanced from the center of the imager chip 732 by a 400 micron diagonal distance, the first grinder 736 has a diameter of 800 microns and reaches a minimum distance of 400 microns from the corners of the imager chip 732, and the second grinder 738 has a diameter of 300 microns and reaches a minimum distance of 150 microns from the sides of the imager chip 732.

Figure 8:
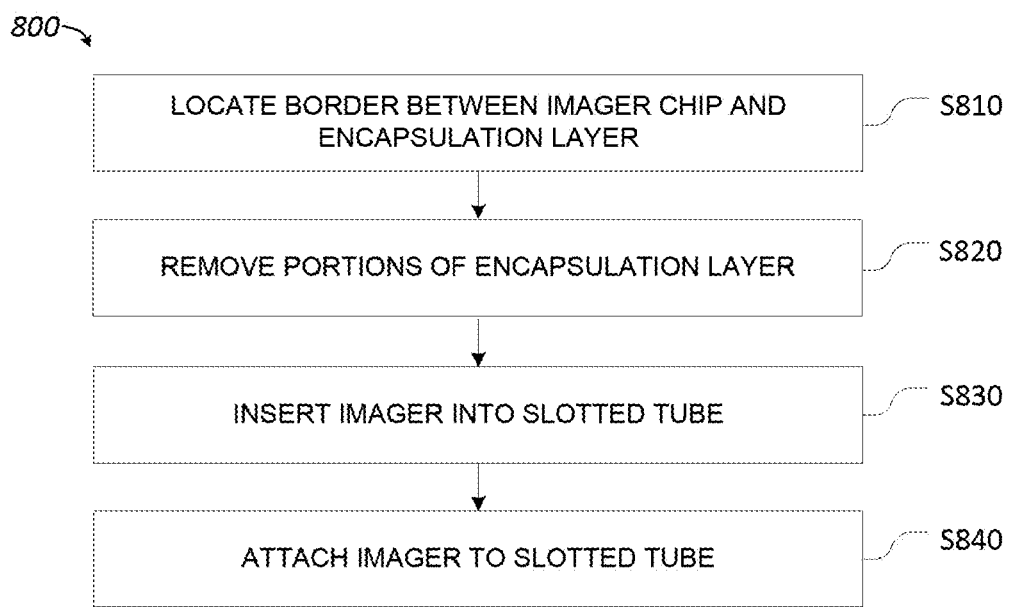
FIG. 8 is a flow-chart describing a method for fabricating an imaging probe according to an embodiment of the present disclosure.

FIG. 8 is a flow-chart describing a method 800 for fabricating an imaging probe according to an embodiment of the present disclosure. The method 800 includes locating a border between an imager chip and an encapsulation layer of an imager at 5810, removing portions of the encapsulation layer at 5820, inserting the imager into a slotted tube at 5830, and attaching the imager to the slotted tube at 5840.

At 5810, the border between the imager chip and the encapsulation layer can be located using any of a variety of methods. For example, the border can be located by performing a CT scan of the imager, because the imager chip and the encapsulation layer have different levels of x-ray attenuation. In another example, the border can be located by locating a center of the imager chip, and measuring predetermined dimensions of the imager chip from the center.

Using the border located at 5810, portions of the encapsulation layer are removed without removing portions of the imager chip at 5820. For example, the encapsulation layer is trimmed by sawing the encapsulation layer, cutting the encapsulation layer, grinding the encapsulation layer, or a combination thereof. In various embodiments, a minimum thickness of the encapsulation layer on the imager chip is about 10 nanometers or less. When the imager chip has a polygonal cross-section, the corners of the imager chip are adjacent to the outer corners of the trimmed encapsulation layer. Once the portions of the encapsulation layer are removed, the imager has a plurality of corners remaining.

At 5830, the trimmed imager is inserted into a slotted tube. Specifically, the corners of the imager are placed into slots of the slotted tube. In some embodiments, a plurality of light guides are also placed into slots of the slotted tube.

The trimmed imager is attached to the slotted tube at 5840. For example, the trimmed imager is glued to the slotted tube by inserting a glue into the slots with the corners of the imager. Suitable glues include, for example, epoxy-based adhesives, silicone-based adhesives, ultraviolet (UV)-cured adhesives, epoxy-polyurethane blend adhesives, cyanoacrylate-based adhesives, or a combination thereof.

Various embodiments of the present disclosure relate to an imaging probe including a trimmed imager. An imaging probe according to an embodiment of the present disclosure can be used in a variety of minimally invasive surgical devices. Examples of minimally invasive devices are found in, for example, U.S. application Ser. No. 15/261,743, entitled "IMAGING NEEDLE APPARATUS" and published as U.S. Pub. No. 2017/0070654; U.S. application Ser. No. 15/444,180, entitled "VIDEO NEEDLE SYRINGE" and published as U.S. Pub. No. 2017/0245890; U.S. application Ser. No. 15/721,376, entitled "VIDEO NEEDLE SYRINGE" and published as U.S. Pub. No. 2018/0084986; and U.S. application Ser. No. 15/036,609, entitled "IMAGING NEEDLE APPARATUS" and published as U.S. Pub. No. 2017/0100020; all of which are incorporated by reference herein in their entirety.

Figure 9A:
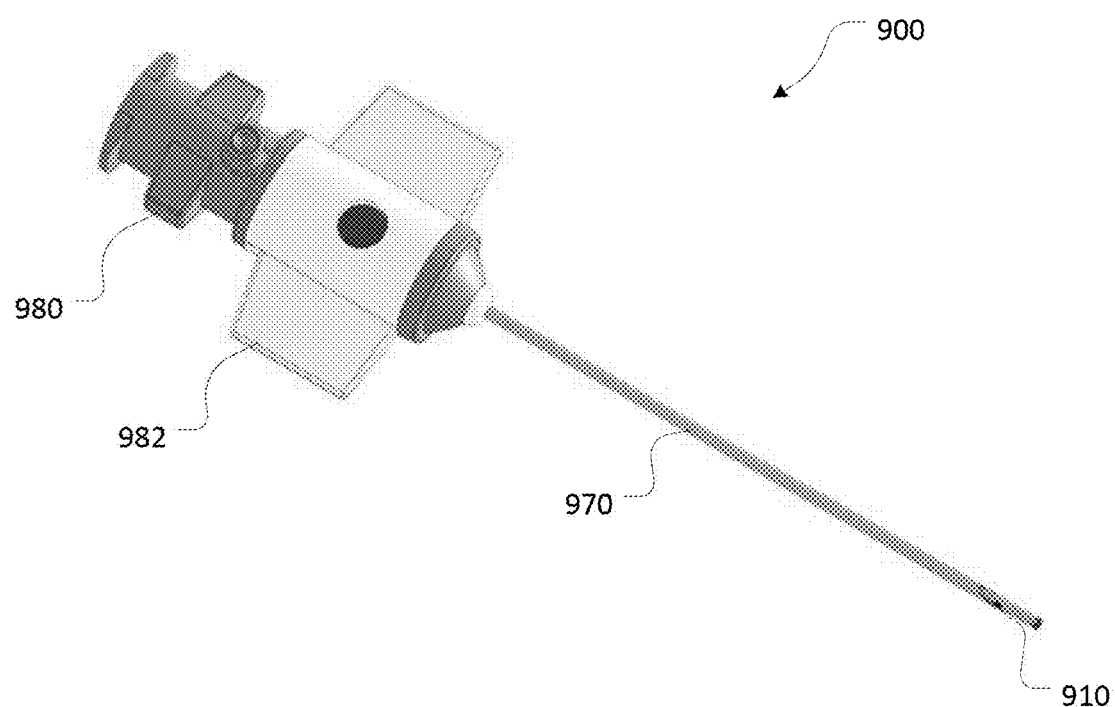
FIGS. 9A and 9B illustrate an imaging needle according to an embodiment of the present disclosure.
Figure 9B:
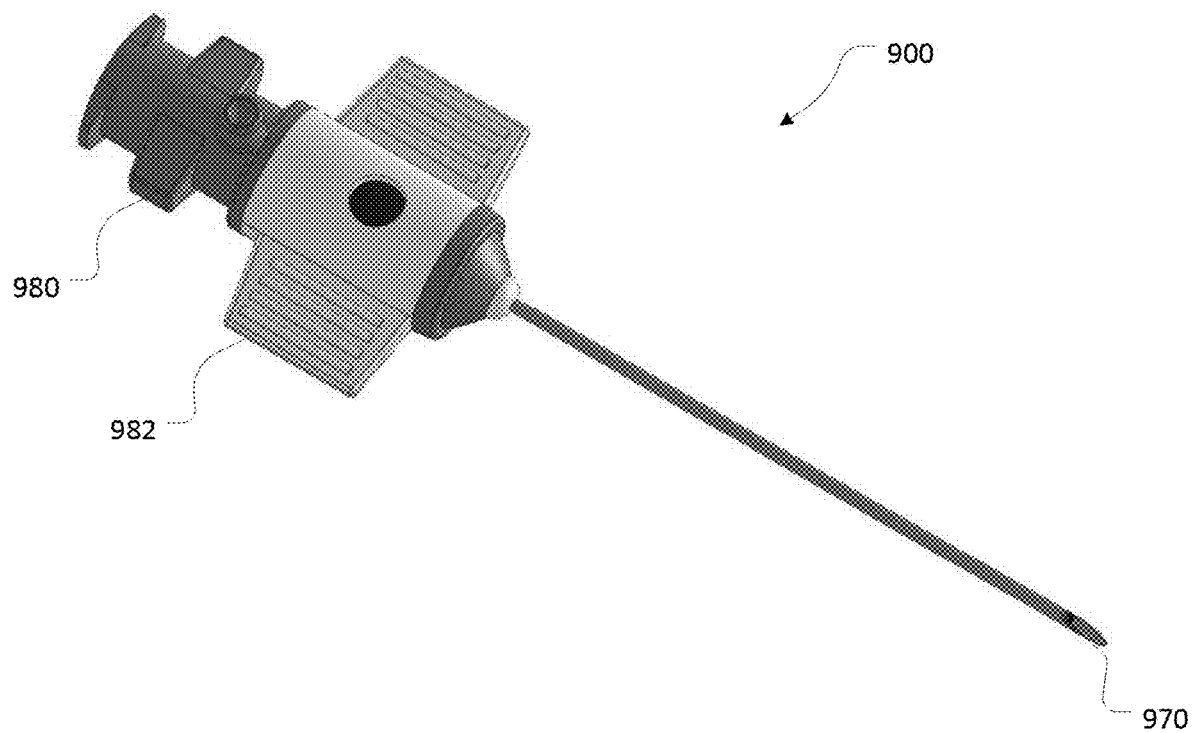

FIGS. 9A and 9B illustrate an imaging needle 900 according to an embodiment of the present disclosure. The imaging needle 900 includes an imaging probe 910, a needle 970, and a bulb 980.

The imaging probe 910 is retractable with respect to the needle 970, and is configured to be inserted underneath the skin of a patient, and image areas of interest. For example, when a user operates a hub 982 on the bulb 980, a distal end of the imaging probe 910 can be retracted from a distal end of the needle 970, or extend from the distal end of the needle 970.

In some embodiments, the imaging probe 910 is the imaging probe 100 described above with reference to FIGS. 1A and 1B. That is, the imaging probe 910 includes an imager and a plurality of light guides disposed in a slotted tube, such that corners of the imagers and the light guides are disposed within slots in the slotted tube. The slots of the tube and the imager are located at a distal end of the imaging probe 910, in various implementations.

The imaging probe 910 can further include one or more holes that are located proximate to the imager. These holes are configured to expel fluid when the imaging probe 910 is in an extended position. In some embodiments, the holes are configured to deliver a therapeutic fluid to an area of interest within a patient. For example, the holes expel a stem cell solution stored inside of the imaging probe 910.

The needle 970 is configured to pierce soft tissue, so that the imaging probe 910 can be inserted into an area of interest underneath a patient's skin. The needle 970 is disposed around the imaging probe 910. A distal end of the needle 970 is sharp, and capable of piercing soft tissue.

The bulb 980 supports the imaging probe 910 and the needle 970, and is configured to be held and operated by a user, e.g., a surgeon. The bulb 980 is further configured to exert pressure on the space inside of the imaging probe 910 where the fluid is stored inside of the imaging probe 910, in order to cause the fluid to be expelled through the holes in the imaging probe 910. The bulb 980 also includes the hub 982, which is operated by the user in order to extend and/or retract the imaging probe 910. The imaging probe 910 and the needle 970 extend from the bulb 980.

Figure 10A:
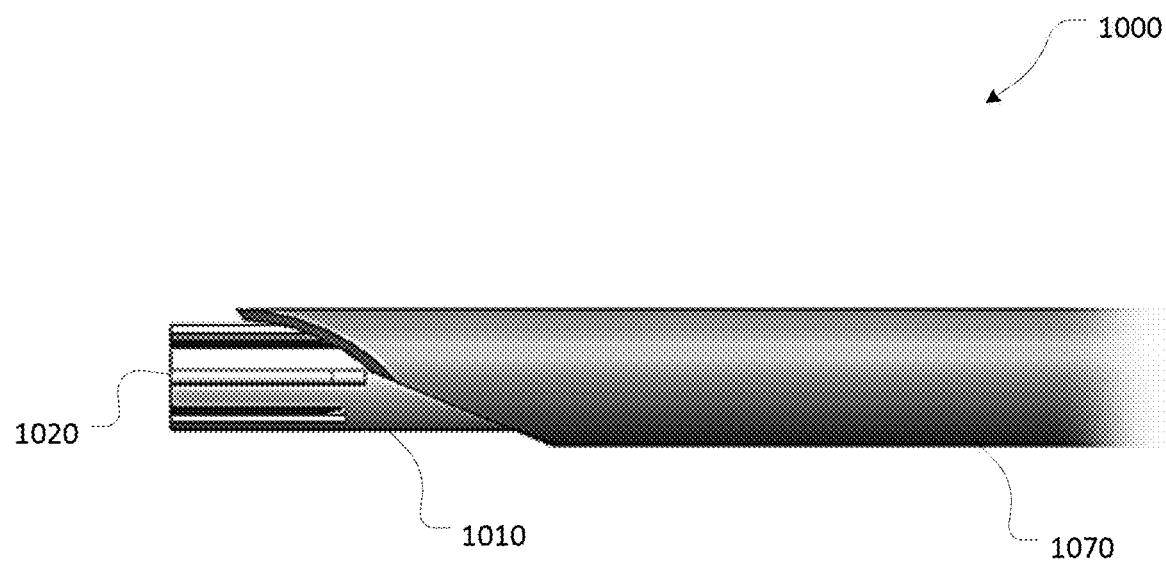
FIGS. 10A and 10B illustrate a distal end of an imaging needle according to an embodiment of the present disclosure.
Figure 10B:
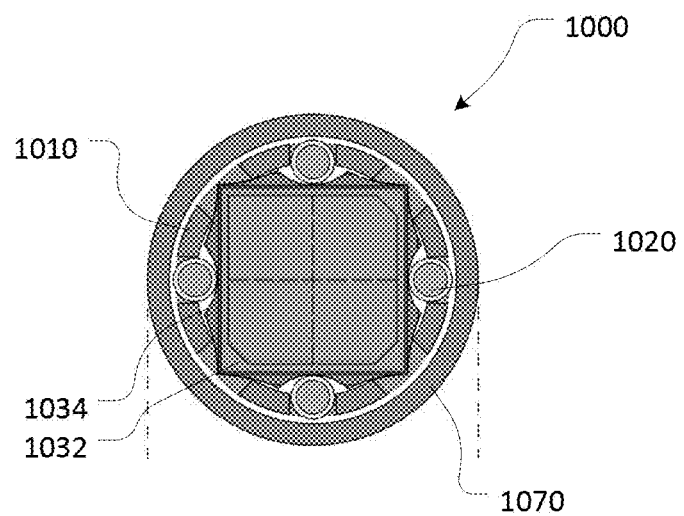

FIGS. 10A and 10B illustrate a distal end 1000 of an imaging needle according to an embodiment of the present disclosure. The distal end 1000 of the imaging needle includes a needle 1070 and a retractable imaging probe extending from the needle 1070.

The imaging probe includes a slotted tube 1010, a plurality of light guides 1020, and an imager 1030. The imager 1030 has a polygonal cross-section. For example, the imager 1030 has a square cross-section. A plurality of corners of the imager 1030 are disposed in first slots in the slotted tube 1010. The light guides 1020 are disposed in second slots in the slotted tube.

The present disclosure relates to an imaging probe with a tube disposed around a trimmed imager. The imaging probe can be used to perform a minimally invasive surgical procedure for both diagnosing and treating tissues in a patient's body. For example, the imaging probe can be disposed in a needle as part of a minimally invasive surgical device that can be used as an alternative to an arthroscope.

In an embodiment, the minimally invasive surgical device is significantly smaller than a traditional arthroscope because the encapsulation layer of the imager is selectively trimmed, which reduces the width of the imager. For example, a needle syringe including the trimmed imager mounted in a slotted tube can have a puncture area that is about 72% of the puncture area of a needle syringe including an untrimmed imager in a slotted tube. As a result, the device can be used to perform less invasive imaging and treatment procedures in subdermal spaces than traditional arthroscopy.

In an embodiment, the device can be used to both take pictures of a target and to treat the target. For example, the device can be used to take a video of a subdermal tissue, and to deliver a liquid treatment to the tissue. As a result, the apparatus can reduce the cost of minimally invasive treatments.

By integrating diagnostic and therapeutic functions into the same device, embodiments of the present disclosure can reduce the number of incisions for performing a procedure, reduce the damage caused by threading a device through an incision by reducing the number of times equipment is inserted through the incision, and reduce the number of devices required to perform the procedure. As a result, embodiments of the present disclosure can be less invasive and less expensive than traditional surgical tools.

The above specification, examples, and data provide a description of the manufacture and use of the composition of various embodiments of the invention. Since many embodiments of the invention can be made without departing from the spirit and scope of the invention, the invention also resides in the claims hereinafter appended.

What is claimed is:

1. An apparatus, comprising:
    a trimmed imager including an imager chip and an encapsulation layer, the imager chip have a polygonal cross-section with a plurality of first corners, the encapsulation layer being disposed around the polygonal cross-section of the imager chip and having a plurality of second corners, a number of the second corners of the encapsulation layer being greater than that of the first corners of the imager chip; and
    a slotted tube having a wall, the wall having a plurality of first slots, a portion of the second corners of the encapsulation layer being disposed inside the plurality of first slots in the wall of the slotted tube,
    wherein the first corners of the imager chip are disposed in the plurality of first slots in the wall of the slotted tube, and the encapsulation layer has a plurality of curved sides, an adjacent pair of the plurality of curved sides meeting at a corresponding one of the second corners of the encapsulation layer.

2. The apparatus of claim 1, wherein the imager chip has a square cross-section.

3. The apparatus of claim 1, wherein the imager chip is configured to capture digital images through a distal end of the slotted tube.

4. The apparatus of claim 1, wherein the adjacent pair of the plurality of curved sides of the encapsulation layer substantially meet at a corresponding one of the first corners of the imager chip.

5. The apparatus of claim 1, further comprising:
    a plurality of light guides,
    wherein the slotted tube includes a plurality of second slots, the plurality of light guides being disposed in the plurality of second slots, respectively.

6. The apparatus of claim 1, further comprising:
    an interposer disposed in the slotted tube and proximate to the trimmed imager, the interposer being configured to supply a voltage to the imager chip and to receive image data from the imager chip.

7. The apparatus of claim 1, further comprising:
    a lens disposed on a distal end of the slotted tube, the lens being configured to focus light on the imager chip.

8. The apparatus of claim 1, wherein each of the plurality of curved sides of the encapsulation layer is concave.

9. A method, comprising:
    locating a border between an imager chip and an encapsulation layer, an imager including the imager chip and the encapsulation layer;
    generating a trimmed imager by removing portions of the encapsulation layer without removing portions of the imager chip using the located border; and
    inserting the trimmed imager into a slotted tube having a wall, the wall having a plurality of slots, a plurality of first corners of the trimmed imager being disposed inside the plurality of slots in the wall of the slotted tube.

10. The method of claim 9, wherein locating a border between the imager chip and the encapsulation layer includes performing a computed tomography (CT) scan on the imager, the imager chip and the encapsulation layer having different levels of x-ray attenuation.

11. The method of claim 9, wherein locating a border between the imager chip and the encapsulation layer includes locating a center of the imager chip, and measuring a predetermined dimension of the imager chip from the located center.

12. The method of claim 9, wherein generating the trimmed imager by removing portions of the encapsulation layer without removing portions of the imager chip using the located border includes cutting portions of the encapsulation layer, sawing portions of the encapsulation layer, grinding portions of the encapsulation layer, or a combination thereof.

13. The method of claim 9, wherein generating the trimmed imager by removing portions of the encapsulation layer without removing portions of the imager chip using the located border includes:
   removing first portions of the encapsulation layer by cutting the encapsulation layer without cutting the imager chip;
   removing second portions of the encapsulation layer by grinding the encapsulation layer with a first grinder without grinding the imager chip; and
   removing third portions of the encapsulation layer by grinding the encapsulation layer with a second grinder without grinding the imager chip, the second grinder having a smaller diameter than the first grinder.

14. The method of claim 13, wherein removing the second portions of the encapsulation layer by grinding the encapsulation layer with the first grinder without grinding the imager chip includes positioning the first grinder a buffer distance from a corner of the located border, and
   wherein removing the third portions of the encapsulation layer by grinding the encapsulation layer with the second grinder without grinding the imager chip includes positioning the second grinder the buffer distance from a side of the located border.

15. The method of claim 14, wherein the buffer distance is about 10 nanometers.

16. The method of claim 9, wherein, after removing the portions of the encapsulation layer, the encapsulation layer has a plurality of second corners a plurality of curved sides, an adjacent pair of the plurality of curved sides meeting at a corresponding one of the second corners of the encapsulation layer, a portion of the second corners of the encapsulation layer being disposed inside the plurality of slots in the wall of the slotted tube.

17. An apparatus, comprising:
   a needle; and
   a probe disposed in the needle, the probe including:
      a trimmed imager including an imager chip and an encapsulation layer, the imager chip have a polygonal cross-section with a plurality of first corners, the encapsulation layer being disposed around the polygonal cross-section of the imager chip and having a plurality of second corners, a number of the second corners of the encapsulation layer being greater than that of the first corners of the imager chip; and
      a slotted tube having a plurality of first slots, a portion of the second corners of the encapsulation layer being disposed inside the plurality of first slots,
   wherein the encapsulation layer has a plurality of curved sides, an adjacent pair of the plurality of curved sides meeting at a corresponding one of the second corners of the encapsulation layer.

18. The apparatus of claim 17, wherein the probe further includes a plurality of light guides, and
   wherein the slotted tube includes a plurality of second slots, the plurality of light guides being disposed in the plurality of second slots, respectively.

19. The apparatus of claim 17, further comprising:
   a bulb attached to a proximal end of the needle and a proximal end of the probe; and
   a hub disposed on the bulb, the hub being configured to extend and retract a distal end of the probe from a distal end of the needle.

20. The apparatus of claim 18, wherein the slotted tube has a wall and the plurality of the first slots and the plurality of the second slots are provided in the wall,
   wherein the first corners of the imager chip are disposed in the plurality of the first slots in the wall of the slotted tube, and
   wherein the plurality of light guides are disposed in the plurality of the second slots in the wall of the slotted tube.

* * * * *